United States Patent [19]

Araki et al.

[11] Patent Number: 4,469,907

[45] Date of Patent: Sep. 4, 1984

[54] SELECTIVE HYDROGENATION METHOD FOR HYDROCARBONS

[75] Inventors: Masashi Araki; Yasuhiko Higashio, both of Chiba, Japan

[73] Assignee: Sumitomo Chemical Company, Limited, Osaka, Japan

[21] Appl. No.: 471,401

[22] Filed: Mar. 2, 1983

[30] Foreign Application Priority Data

Mar. 2, 1982 [JP] Japan .................................. 57-33652

[51] Int. Cl.$^3$ ............................................... C07C 5/08
[52] U.S. Cl. .................................. 585/259; 585/265; 585/275; 585/277; 208/143
[58] Field of Search ............... 585/259, 265, 275, 277; 208/143, 216

[56] References Cited

U.S. PATENT DOCUMENTS

| | | | |
|---|---|---|---|
| 2,993,855 | 7/1961 | Fear | 208/143 |
| 3,898,298 | 9/1975 | Desiderio et al. | 585/259 |
| 4,347,392 | 8/1983 | Cosyns et al. | 585/259 |

*Primary Examiner*—Curtis R. Davis
*Attorney, Agent, or Firm*—Sughrue, Mion, Zinn, Macpeak and Seas

[57] ABSTRACT

A selective hydrogenation method for highly saturated hydrocarbons by bringing a mixture of hydrocarbons of low hydrogenation degree having 4 or more carbon atoms containing the highly saturated hydrocarbons in the presence of a catalyst using a fixed bed reaction vessel, which comprises supplying a hydrogen gas in a state of plural splits along the flow direction of the fixed bed reaction vessel is disclosed. In accordance with this mehtod, only the highly unsaturated hydrocarbons are selectively hydrogenated without being accompanied by isomerization of olefins.

9 Claims, No Drawings

SELECTIVE HYDROGENATION METHOD FOR HYDROCARBONS

FIELD OF THE INVENTION

This invention relates to a selective hydrogenation method for dienes and acetylenes into monoenes. More particularly, the invention relates to a method of coverting only unsaturated hydrocarbons having two or more double bonds and/or one or more triple bonds in each molecule (hereinafter, are referred to as highly unsaturated hydrocarbons) into corresponding hydrocarbons of low unsaturation degree without being accompanied by isomerization of the double bonds by bringing a mixture of unsaturated hydrocarbons having 4 or more carbon atoms containing the highly unsaturated hydrocarbons into contact with hydrogen in the presence of a catalyst.

BACKGROUND OF THE INVENTION

A method is generally known wherein a mixture of unsaturated hydrocarbons having 4 or more carbon atoms containing highly unsaturated hydrocarbons is reacted with hydrogen in the presence of a hydrogenation catalyst to selectively hydrogenate the highly unsaturated hydrocarbons into corresponding hydrocarbons of low unsaturation degree. For example, a method of selectively hydrogenating dienes and acetylenes only by reacting a mixture of unsaturated hydrocarbons having 4 carbon atoms containing the dienes such as butadiene, methylallene, etc.; acetylenes such as dimethylacetylene, ethylacetylene, vinylacetylene, etc.; and monoolefins such as 1-butene, 2-butene, isobutene, etc., with hydrogen in the presence of a hydrogenation catalyst such as palladium, platinum, nickel, etc., has been industrially employed.

However, in such a known selective hydrogenation method, there is a demerit that intramolecular transfer of double bonds easily occurs simultaneously with the selective hydrogenation to highly unsaturated bonds such as two or more double bonds and one or more triple bonds, whereby the composition of reaction product is greatly changed. For example, when a selective hydrogenation reaction of unsaturated hydrocarbons having 4 carbon atoms containing, for example, butadienes and butynes is performed, isomerization of 1-butene into 2-butene easily occurs simultaneously with the selective hydrogenation of butadienes and butynes into butenes, whereby the concentration of 1-butene in the reaction product is greatly reduced.

1-Butene is important as a monomer for producing polyolefins. Hence, from the viewpoint of effective utilization of 1-butene in a mixture of hydrocarbons having 4 carbon atoms, the development of a method capable of selectively hydrogenating highly unsaturated hydrocarbons only without being accompanied by isomerization has been strongly demanded.

SUMMARY OF THE INVENTION

As the result of various investigations on the selective hydrogenation method for highly unsaturated hydrocarbons only without being accompanied by the foregoing isomerization of olefins, the inventors have succeeded in attaining this invention.

That is, it has been discovered that in a method of selectively hydrogenating highly unsaturated hydrocarbons by bringing hydrocarbons of low unsaturation degree having 4 or more carbon atoms containing the foregoing highly unsaturated hydrocarbons into contact with hydrogen in the presence of a catalyst using a fixed bed reaction vessel, the selective hydrogenation reaction only of the highly unsaturated hydrocarbons proceeds with the isomerization of olefins being not substantially accompanied by supplying a hydrogen gas in a state of plural splits along the flow direction of the fixed bed reaction vessel.

DESCRIPTION OF THE PREFERRED EMBODIMENT

As the manner of supplying a hydrogen gas in a state of plural splits, though the hydrogen gas may be supplied through plural gas inlets disposed along the flow direction of a fixed bed reaction vessel packed with a catalyst, a method in which a catalyst layer packed in a fixed bed reaction vessel is split into several layers along the flow direction of the reaction vessel and the hydrogen gas is separately supplied to each zone containing no catalyst between the catalyst layers is generally useful.

Also, a method in which plural fixed bed reaction vessels are connected in series and a hydrogen gas is separately supplied to each fixed bed reaction vessel is a preferred embodiment for practicing the method of this invention. In the case of connecting plural fixed bed reaction vessels in series, a heat exchanger, etc., may be disposed between the reaction vessels, whereby the reaction temperature, reaction pressure, etc. of each fixed bed reaction vessel thus connected in series can be independently controlled at preferred conditions for performing the reaction.

In the method of this invention, it is necessary to supply a hydrogen gas in a state of plural splits along the flow direction of a fixed bed reaction vessel. As the number of splits of hydrogen gas to be supplied is larger, the result of the reaction becomes better but, in this case, the process of the reaction becomes more complicated and the operation becomes more troublesome. Therefore, it is preferred to supply the hydrogen gas in a state of two or three splits.

The proportion of hydrogen gas supplied in each split varies with the position of the inlet thereof and there is no particular restriction therein. However, it is preferred that the amount of hydrogen gas in the 2nd split or the later split or splits be 5 to 100% of the amount of hydrogen gas in the previous split. By supplying a hydrogen gas to the fixed bed reaction vessel in a split state in the foregoing proportion, the selective hydrogenation of highly unsaturated hydrocarbons can be performed, without substantial isomerization of the olefins.

There is no particular restriction about the position for supplying the splits of hydrogen gas but usually it is so disposed that a part of hydrogen gas is split before the hydrocarbons are brought into contact with a catalyst and the 2nd and later inlet portions are disposed along the flow direction of the fixed bed reaction vessel with an almost equal interval. Also, in the case of performing the reaction using a fixed bed reaction vessel havng a plural split catalyst layer disposed along the flow direction or plural fixed bed reaction vessels connected with each other in series along the flow direction, the size of the respective catalyst-packed layers or the size of the respective fixed bed reaction vessels connected with each other in series is usually selected to be substantially the same, and the hydrogen gas is split before each catalyst layer or each fixed bed reaction vessel. However, as the case may be, the size of these catalyst-packed layers or fixed bed reaction vessels may be different from each other.

In the case of performing the hydrogenation reaction of hydrocarbons using a fixed bed reaction vessel, the whole necessary amount of hydrogen gas is usually supplied to the inlet of the reaction vessel together with the starting hydrocarbons. However, in a method of selectively hydrogenating highly unsaturated hydrocarbons by bringing a mixture of hydrocarbons of low unsaturation degree having 4 or more carbon atoms containing the highly unsaturated hydrocarbons into contact with hydrogen in the presence of a catalyst using a fixed bed reaction, when the hydrogenation reaction is performed by supplying a hydrogen gas to only the inlet of the reaction vessel, intramolecular transfer of double bonds easily occurs simultaneously with the occurrence of the hydrogenation reaction of the highly unsaturated hydrocarbons.

As a result of various investigations on the selective hydrogenation method for highly unsaturated hydrocarbons without being accompanied by such intramolecular transfer of double bonds, it has been surprisingly found that by supplying a hydrogen gas in a state of plural splits along the flow direction of fixed bed reaction vessel, only the highly unsaturated hydrocarbons are selectively hydrogenated without being accompanied by the intramolecular transfer of double bonds, resulting in this invention.

As a method of selectively hydrogenating highly unsaturated hydrocarbons without being accompanied by isomerization of olefins, there are proposed a method of performing the selective hydrogenation reaction using an $H_2$ gas containing a large amount of C gas (Japanese Patent Publication No. 39808/71); a method of performing the hydrogenation in a vapor-liquid mixed phase at the first step and then performing the hydrogenation in a liquid phase at the 2nd step (Japanese Patent Publication No. 16082/77); and a method of using a specific catalyst (Japanese Patent Publication No. 28922/75 and German Pat. No. 2,108,276), etc. However, these known methods each have faults that it is necessary to use an expensive CO gas, that it is necessary to use a specific catalyst, and that the process becomes complicated.

On the other hand, this invention provides a method of selectively hydrogenating highly unsaturated hydrocarbons only, without being accompanied by isomerization of olefins in a relatively simple manner by supplying a hydrogen gas in a state of plural splits along the flow direction of a fixed bed reaction vessel. Hence, the invention is quite meaningful from the industrial viewpoint.

In the method of this invention, any types of isothermal-type reaction vessels or heat insulating-type reaction vessels can be used as the fixed bed reaction vessel, or a combination of both types can also be employed.

As the catalyst used in this invention, a nickel catalyst, a palladium catalyst, a platinum catalyst, etc. are useful, with the palladium catalyst being preferred. As the palladium catalyst, there are palladium black, palladium-on-carbon, palladium-on-alumina, etc. Usually, a catalyst having 0.02 to 2% by weight of palladium supported on a carrier such as alumina, etc. is used.

As a mixture of hydrocarbons of low unsaturation degree having 4 or more carbon atoms containing highly unsaturated hydrocarbons used in the method of this invention, there are a mixture of $C_4$ hydrocarbons composed of so-called $C_4$ fractions such as butadiene, butane, butene, etc., obtained by steam cracking of naphtha, etc.; a mixture of $C_4$ hydrocarbons called spent BB fractions, i.e., the foregoing $C_4$ fractions from which a major part of butadiene has been removed by extraction; a mixture of $C_4$ hydrocarbons mainly composed of 1-butene and 2-butene obtained by further removing isobutylene from the spent BB fractions; and a mixture of hydrocarbons mainly composed of $C_5$ hydrocarbons such as isoprene, etc.

As highly unsaturated hydrocarbons present in these hydrocarbon mixtures, there are propadiene, methylacetylene, 1,2-butadiene, 1,3-butadiene, ethylacetylene, vinylacetylene, 1,3-pentadiene, etc.

The reaction mode in the method of this invention may be a liquid phase, a vapor phase, or a vapor-liquid mixed phase such as a trickle phase. The reaction in a vapor phase is, however, preferred in this invention. In the case of performing the reaction using plural fixed bed reaction vessels connected with each other in series, the reaction mode in the respective fixed bed reaction vessels may be different.

When the reaction is performed in a vapor phase in the method of this invention, a gaseous hydrocarbon mixture emerging from the top of a distilling column may be directly supplied to the hydrogenation reaction vessel. Also, a gaseous mixture after the hydrogenation reaction may be supplied to a distilling column in a gaseous state without being liquified to perform the separation of hydrocarbons. By this manner, process can be simplified and an energy required can be saved.

As the hydrogenation reaction employed in the method of this invention, the reaction temperature is usually $-20°$ C. to $150°$ C. and the reaction pressure is usuallyatmospheric pressure to 50 atms. It is, however, preferred that the reaction temperature be 20° to 100° C. and the reaction pressure be 2 to 20 atms. Also, the total amount of hydrogen gas supplied is in the range of 1 to 3 moles, preferably 1.1 to 2.0 moles per mole of the highly saturated hydrocarbons in the starting hydrocarbon mixture.

The method of this invention will be further explained by referring to the following examples but the scope of this invention is not restricted by these examples.

EXAMPLE 1

A $C_4$ hydrocarbon mixture having the composition shown in Table 1 was used as the starting material. Also, a catalyst having 0.3% by weight of palladium supported on an alumina carrier was used. The palladium-on-alumina catalyst was packed in each of two reaction tubes of 20 mm in inside diameter in an amount of 75 ml. The reaction tubes were connected with each other in series and placed vertically. Under the conditions of a reaction temperature of 50° C. and a reaction pressure of 4 atms., the foregoing $C_4$ hydrocarbon mixture was introduced into the first reaction tube at a rate of 1.18 kg/hr. and also a hydrogen gas was introduced into the inlet of the first reaction tube at a rate of 7.5 liters (calculated as NTP)/hr. and into the inlet of the 2nd reaction tube at a rate of 1.8 liters (calculated as NTP)/hr. to perform the vapor-phase hydrogenation. The composition of the reaction product thus obtained is shown in Table 1.

TABLE 1

| Compound | Composition of Starting Material (mole %) | Composition of Product (mole %) |
| --- | --- | --- |
| Propane, Propadiene | 0.02 | 0.29 |
| i-Butane | 4.73 | 4.74 |
| n-Butane | 11.89 | 11.89 |
| i-Butene | 46.83 | 46.84 |
| 1-Butene | 24.21 | 24.36 |
| 2-Butene | 11.16 | 11.87 |
| 1,3-Butadiene | 0.76 | 0 |
| Propadiene | 0.26 | 0 |
| 1,2-Butadiene | 0.05 | 0 |
| Vinylacetylene | 0.08 | 0 |

By supplying the hydrogen gas in a split state, butadiene as well as other dienes and acetylenes could be completely hydrogenated without being accompanied by a loss of 1-butene as shown in Table 1.

EXAMPLES 2 TO 4 AND COMPARATIVE EXAMPLE 1

The experiment was performed using the same catalyst and reaction apparatus as in Example 1. Also, the hydrogenation was performed under the same reaction conditions as in Example 1 except that the hydrogen gas was supplied at the rates as shown in Table 2. The results obtained are shown in Table 2.

TABLE 2

|  | (A)* | (B)* | (C)* | (D)* |
| --- | --- | --- | --- | --- |
| Example 2 | 8.5 | 1.0 | 12 | 0.1 |
| Example 3 | 5.5 | 4.9 | 9 | 0.8 |
| Example 4 | 3.5 | 7.7 | 21 | 3.2 |
| Comparative Example 1 | 13.8 | 0 | 16 | 14.5 |

(A)*Hydrogen supply rate at the inlet of the first reaction tube in liter (cald. as NTP)/hr.
(B)*Hydrogen supply rate at the inlet of the 2nd reaction tube in liter (cald. as NTP)/hr.
(C)*Residual amount of butadiene (mole ppm).
(D)*Conversion ratio of 1-butene (%).

EXAMPLE 5 AND COMPARATIVE EXAMPLE 2

By using the same catalyst and reaction apparatus as in Example 1, a liquid-phase hydrogenation reaction was performed at a reaction temperature of 40° C. and a pressure of 20 atms. Then, the same starting material and hydrogen gas as in Example 1 were supplied to the respective reaction tubes at the supply rates shown in Table 3. The results obtained are shown in Table 3.

TABLE 3

|  | Starting Material Supply Rate (kg/hr.) | (A)* | (B)* | (C)* | (D)* |
| --- | --- | --- | --- | --- | --- |
| Example 5 | 1.77 | 11 | 4 | 18 | 4.2 |
| Comparative Example 2 | 1.77 | 20 | 0 | 17 | 18.3 |

(A)*, (B)*, (C)* and (D)* are the same as in Table 2.

While the invention has been described in detail and with reference to specific embodiments thereof, it will be apparent to one skilled in the art that various changes and modifications can be made therein without departing from the spirit and scope thereof.

What is claimed is:

1. A method of selectively hydrogenating highly unsaturated hydrocarbons by bringing a mixture of hydrocarbons of low unsaturated degree having 4 or more carbon atoms containing said highly unsaturated hydrocarbons into contact with hydrogen in the presence of a catalyst using a fixed bed reaction vessel, which comprises supplying said hydrogen gas in a state of plural splits along the flow direction of said fixed bed reaction vessel.

2. A method as claimed in claim 1, wherein the flow rate of hydrogen gas in the 2nd split or later split or splits along the flow direction of said fixed bed reaction vessel is 5 to 100% of the previous split.

3. A method as claimed in claim 1 or 2, wherein using a fixed bed reaction vessel containing plural catalyst layers split into plural zones along the flow direction, hydrogen gas is independently supplied to each zone.

4. A method as claimed in any of claims 1, 2, or 3, wherein the hydrogenation reaction is performed in a vapor phase.

5. A method as claimed in any of claims 1, 2, or 3, wherein the total amount of hydrogen gas supplied is 1.1 to 2.0 moles per mole of said highly unsaturated hydrocarbons in the starting hydrocarbon mixture.

6. A method as claimed in any of claims 1 to 5, wherein a palladium catalyst is used as the catalyst.

7. A method of selectively hydrogenating highly unsaturated hydrocarbons by bringing a mixture of hydrocarbons of low unsaturation degree having 4 or more carbon atoms containing said highly unsaturated hydrocarbons into contact with hydrogen in the presence of a catalyst using a fixed bed reaction vessel, which comprises performing the hydrogenation reaction in a vapor phase using a palladium catalyst by supplying a hydrogen gas in a state of plural splits along the flow direction of said fixed bed reaction vessel, the total amount of said hydrogen gas supplied being 1.1 to 2.0 moles per mole of said highly unsaturated hydrocarbons.

8. A method of treating a mixture of hydrocarbons of low unsaturation degree having 4 or more carbon atoms with hydrocarbons of high unsaturation degree to hydrogenate said hydrocarbons of high unsaturation degree without isomerizing said hydrocarbons of low unsaturation degree, said method comprising bringing said mixture into contact with hydrogen gas in the presence of a catalyst using a fixed bed reaction vessel, wherein said hydrogen gas is supplied in a state of plural splits along the flow direction of said fixed bed reaction vessel.

9. The method of claim 1 wherein said hydrocarbons of low unsaturation degree comprise mainly 1-butene and 2-butene.

* * * * *